United States Patent
Sidebotham

(10) Patent No.: US 11,583,406 B2
(45) Date of Patent: Feb. 21, 2023

(54) HIP STEM PROSTHESIS WITH A POROUS COLLAR TO ALLOW FOR BONE INGROWTH

(71) Applicant: Christopher G. Sidebotham, Mendham, NJ (US)

(72) Inventor: Christopher G. Sidebotham, Mendham, NJ (US)

(73) Assignee: BioMedtrix, LLC, Whippany, NJ (US)

( * ) Notice: Subject to any disclaimer, the term of this patent is extended or adjusted under 35 U.S.C. 154(b) by 50 days.

(21) Appl. No.: 15/965,746

(22) Filed: Apr. 27, 2018

(65) Prior Publication Data

US 2018/0243099 A1 Aug. 30, 2018

Related U.S. Application Data

(63) Continuation of application No. 14/019,374, filed on Sep. 5, 2013, now abandoned.

(60) Provisional application No. 61/790,528, filed on Mar. 15, 2013, provisional application No. 61/697,177, filed on Sep. 5, 2012.

(51) Int. Cl.
*A61F 2/36* (2006.01)
*A61F 2/30* (2006.01)

(52) U.S. Cl.
CPC .......... *A61F 2/3607* (2013.01); *A61F 2/3609* (2013.01); *A61F 2002/3092* (2013.01); *A61F 2002/30769* (2013.01); *A61F 2002/30985* (2013.01); *A61F 2002/3631* (2013.01)

(58) Field of Classification Search
CPC .. A61F 2/32; A61F 2/36; A61F 2/3607; A61F 2/3609; A61F 2/3662; A61F 2/367; A61F 2/3672; A61F 2/3637
See application file for complete search history.

(56) References Cited

U.S. PATENT DOCUMENTS

| | | | |
|---|---|---|---|
| 3,938,198 A * | 2/1976 | Kahn | A61F 2/30907 623/22.15 |
| 4,012,796 A | 3/1977 | Weisman et al. | |
| 4,404,693 A | 9/1983 | Zweymueller | |
| 4,406,023 A * | 9/1983 | Harris | A61F 2/30767 623/23.29 |
| 4,435,854 A * | 3/1984 | Keller | A61F 2/3662 623/23.35 |
| 4,728,334 A * | 3/1988 | Spotorno | A61F 2/30771 623/23.31 |
| 4,840,632 A | 6/1989 | Kampner | |
| 5,019,108 A * | 5/1991 | Bertin | A61F 2/30721 623/23.28 |

(Continued)

FOREIGN PATENT DOCUMENTS

FR    2976789 A1 * 12/2012 ......... A61F 2/30771

OTHER PUBLICATIONS

Cansizoglu, "Mesh Structures with Tailored Properties and Applications in Hip Stems." A dissertation submitted to the Graduate Faculty of North Carolina State University, 2008.

(Continued)

*Primary Examiner* — Marcia L Watkins
(74) *Attorney, Agent, or Firm* — Klarquist Sparkman, LLP

(57) ABSTRACT

A femoral hip implant includes a first end, a second end, and a collar with a porous surface, all fabricated from a single piece of material. The entire area of the collar is porous, and the collar elastically deflects under load to promote bone ingrowth.

15 Claims, 7 Drawing Sheets

(56) References Cited

U.S. PATENT DOCUMENTS

| | | | |
|---|---|---|---|
| 5,066,304 A * | 11/1991 | Crowninshield | A61F 2/3609 623/22.45 |
| 5,108,451 A | 4/1992 | Forte | |
| 5,171,324 A * | 12/1992 | Campana | A61F 2/3662 606/86 R |
| 5,549,705 A * | 8/1996 | Michielli | A61F 2/30724 623/23.37 |
| 5,571,202 A | 11/1996 | Mathys et al. | |
| 5,702,485 A | 12/1997 | Burke et al. | |
| 5,709,020 A * | 1/1998 | Pienkowski | A61F 2/32 29/404 |
| 6,695,884 B1 * | 2/2004 | Townley | A61F 2/40 623/23.26 |
| 7,537,664 B2 | 5/2009 | O'Neill et al. | |
| 7,875,083 B2 | 1/2011 | Sudmann | |
| 2002/0120344 A1 * | 8/2002 | Meulink | A61F 2/3662 623/23.3 |
| 2004/0199260 A1 | 10/2004 | Pope et al. | |
| 2005/0267586 A1 * | 12/2005 | Sidebotham | C22C 14/00 623/22.41 |
| 2006/0015188 A1 | 1/2006 | Grimes | |
| 2006/0147332 A1 * | 7/2006 | Jones | A61F 2/30767 419/8 |
| 2007/0129809 A1 | 6/2007 | Meridew et al. | |
| 2007/0196230 A1 | 8/2007 | Hamman et al. | |
| 2011/0208318 A1 | 8/2011 | Sudmann | |

OTHER PUBLICATIONS

Khouja, "Bone regeneration in Novel Porous Titanium Implants." A dissertation submitted to the Faculty of the School of Dentistry, Indiana University, 2010.

Murr et al., "Next-generation biomedical implants using additive manufacturing of complex, cellular and functional mesh arrays," *Philosophical Transactions of the Royal Society of London A: Mathematical, Physical, and Engineering Sciences* 368(1917): 1999-2032, 2010.

Thomsen et al., "Electron beam-melted, free-form-fabricated titanium alloy implants: Material surface characterization and early bone response in rabbits," *Journal of Biomedical Materials Research Part B: Applied Biomaterials* 90(1): 35-44, 2009.

* cited by examiner

Porous Collar $\sigma = Mc / I$ ultimate material stress = 138,000psi *(Titanium 6Al-4V)*
Porous Titanium 35% Solid *(65% open space)*
ultimate adjusted stress = 48,300psi *(Titanium 6Al-4V)*

Moment of inertia: $I = bd^3/12$  $I = (.310)(.120)^3/12 = 4.46 \times 10^{-5}$ in$^4$ $\sigma = F(x) c / I$
$48,300 = F(.220)(.060) / 4.46 \times 10^{-5}$
$F = 48,300 (4.46 \times 10^{-5}) / (.220)(.060)$
$F = 163$ lbs to fracture porous collar

HIP STEM PROSTHESIS WITH A POROUS COLLAR TO ALLOW FOR BONE INGROWTH

CROSS REFERENCE TO RELATED APPLICATIONS

This application is a continuation of U.S. patent application Ser. No. 14/019,374, filed Sep. 5, 2013, which claims the benefit of U.S. Provisional Application No. 61/697,177, which was filed on Sep. 5, 2012, and U.S. Provisional Application No. 61/790,528, which was filed on Mar. 15, 2013. The previous applications are incorporated herein by reference in their entirety.

FIELD

The present disclosure relates to embodiments of a femoral hip implant.

BACKGROUND

There are two primary methods of fixation for femoral hip implants in total hip replacement. The first method utilizes bone cement to bond the femoral hip implant to the surrounding bone. The second method relies on a press fit between the femoral hip implant and the bone to promote long term stability. Such press fit implants are commonly tapered to resist post-operative subsidence into the bone canal, and can include porous surfaces to promote bone ingrowth. Many press fit implants also include a collar that rests on the calcar area of the femur, acting to restrain subsidence and allow load sharing between the bone and the implant.

SUMMARY

In some embodiments, a bone implant apparatus is provided. The apparatus comprises a first end having a substantially smooth surface to inhibit bone ingrowth, a second end extending from the first end in a non-coaxial fashion with a tapered shape and a surface, at least a portion of which comprises a porous surface to allow bone ingrowth, and a collar located between the first and second end. The collar further comprises a porous surface to allow bone ingrowth into the collar.

In some implementations, a femoral hip implant is provided comprising a first end, the first end having a substantially smooth surface to inhibit bone ingrowth, a second end having a substantially tapered shape and extending from the first end in a non-coaxial fashion, at least a portion of which comprises a porous surface to allow bone ingrowth, and a collar located between the first end and the second end, at least a portion of the collar having a porous surface to allow bone ingrowth. The second end of the femoral hip implant is inserted into a femur, and the femoral hip implant is positioned to subside into the femur until the collar contacts the femur so that the porous surfaces of the second end and the collar are aligned with bone to allow bone ingrowth.

The foregoing and other objects, features, and advantages of the invention will become more apparent from the following detailed description, which proceeds with reference to the accompanying figures.

DETAILED DESCRIPTION

Figure 1:
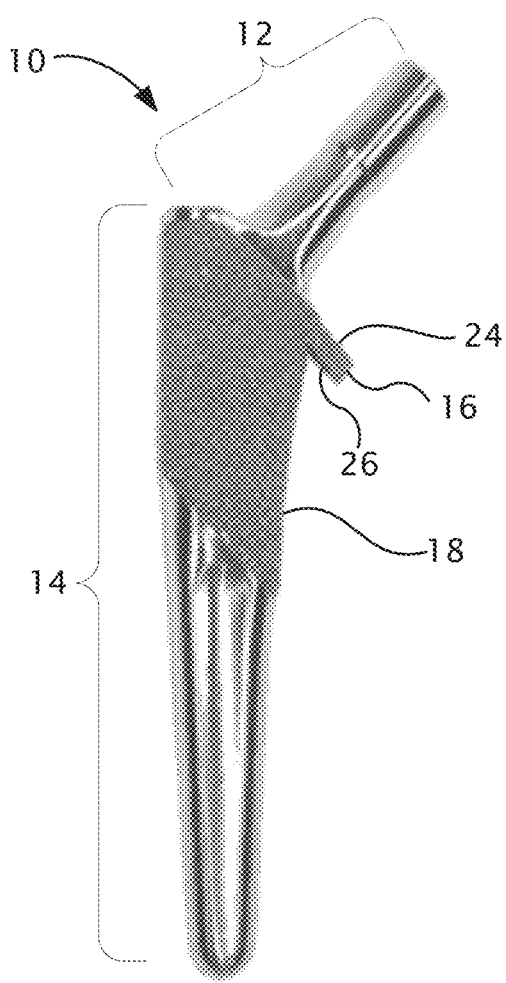
FIG. 1 is a side elevation view of a femoral hip implant.

For purposes of this description, certain aspects, advantages, and novel features of the embodiments of this disclosure are described herein. The disclosed methods, apparatuses, and systems should not be construed as limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

As used in this application and in the claims, the singular forms "a," "an," and "the" include the plural forms unless the context clearly dictates otherwise. Additionally, the term "includes" means "comprises." Further, the terms "coupled"

and "associated" generally mean electrically, electromagnetically, and/or physically (e.g., mechanically or chemically) coupled or linked and does not exclude the presence of intermediate elements between the coupled or associated items absent specific contrary language.

As used herein, the term "porous" means a structure having one or more openings, gaps, or other such surfaces that allow bone to grow into the structure and mechanically interlock with the structure. "Bone ingrowth" refers to the growing of bone into a porous structure in a manner that allows the bone to interlock with the structure.

As used herein, the term "smooth" means a structure lacking in openings, gaps, or other such surfaces that would allow bone to grow into the structure.

A collar with a porous surface acts to stabilize a femoral hip implant by promoting bone ingrowth. However, due to manufacturing limitations, the existing art implants often comprise a solid metal collar with only a textured undersurface. Such textured undersurfaces are ineffective at promoting bone ingrowth, and frequently cause bone resorption under the collar instead. Such bone resorption in turn can cause the femoral hip implant to loosen in some cases, and can result in undesirable revision surgery.

Figure 2:
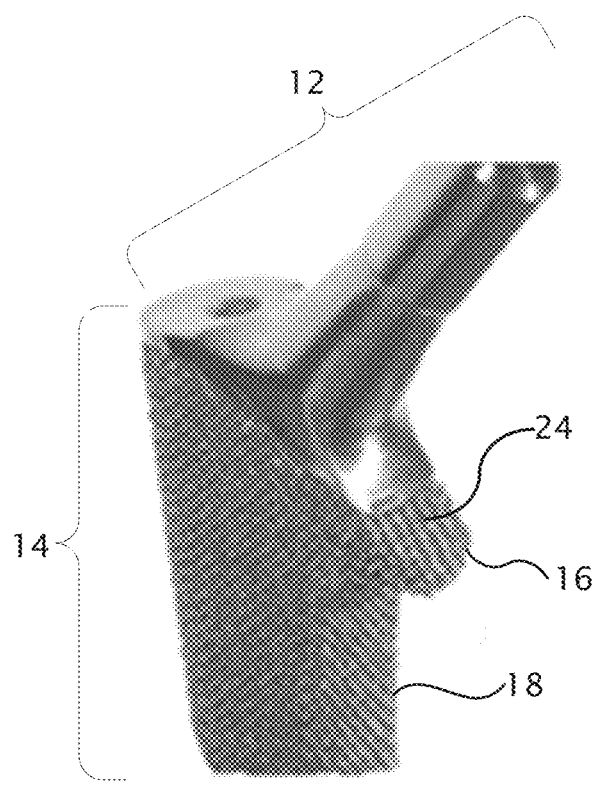
FIG. 2 is an enlarged isometric view of a femoral hip implant.

FIGS. 1-2 depict an embodiment of a femoral hip implant 10. Femoral hip implant 10 comprises a first end 12 (e.g., a proximal portion) having a substantially smooth surface, a second end 14 (e.g., a distal portion) extending distally from the first end 12 in a non-coaxial fashion, and a collar 16 positioned between the first end 12 and the second end 14. In some embodiments, the first end 12 is adapted to receive a femoral head (not shown) and the second end 14 has a tapered shape generally comprising a femoral stem and a porous region 18. In some embodiments, first end 12, second end 14, and the collar 16 are integrally formed from a single piece of material. Additionally, the femoral hip implant 10 can be configured for both human and veterinary applications.

Figure 3:
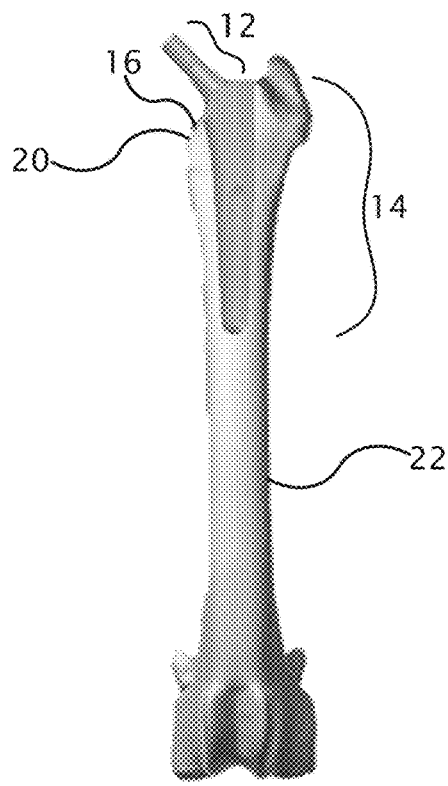
FIG. 3 is a cross-sectional view of a femoral hip implant in a femur.
Figure 4A:
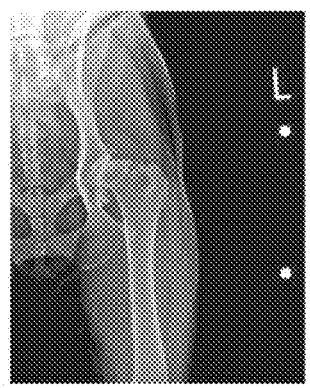
FIG. 4A is a front view showing a hip joint before total hip replacement.
Figure 4B:
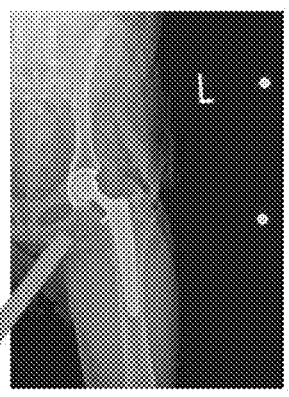
FIG. 4B is a front view of a femoral hip implant showing a gap between a femur and a collar.
Figure 4C:
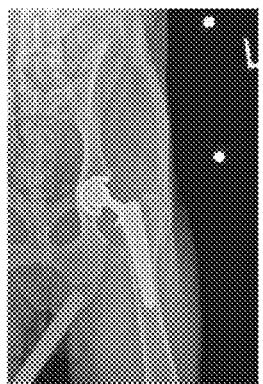
FIG. 4C is a front view of a femoral hip implant showing a collar in contact with a femur.
Figure 4D:
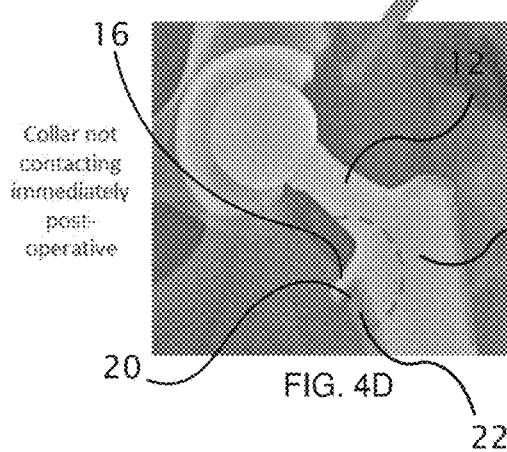
FIG. 4D is a magnified view of FIG. 4B.
Figure 4E:
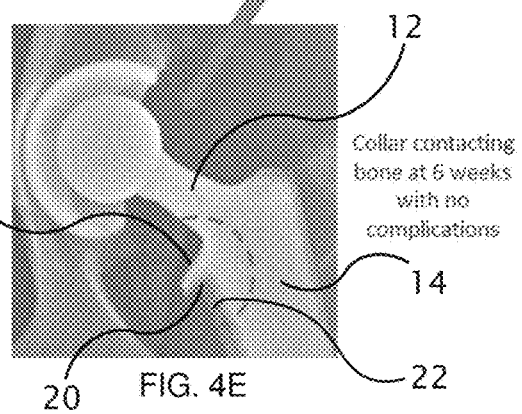
FIG. 4E is a magnified view of FIG. 4C.

The collar 16 can comprise a substantially semicircular projection from second end 14 generally normal to the first end 12, as shown in FIGS. 1-2. In this configuration, the collar 16 can contact the hard calcar area 20 of the femur 22, as shown in FIGS. 3 and 4E, allowing the femoral hip implant 10 to transfer force to the bone when loaded. Additionally, the collar 16 can prevent the femoral hip implant 10 from subsiding into the femur 22 by contacting the calcar area 20 of the femur 22 to arrest motion of the femoral hip implant 10 into the bone canal.

Collar 16 can comprise a top surface 24 and a bottom surface 26, as shown in FIGS. 1-2. In some cases, the bottom surface 26 of the collar 16 will not contact the calcar area 20 of the femur 22 when the femoral hip implant 10 is first implanted. Rather, the femoral hip implant 10 will generally achieve a sufficiently tight press fit before it impacts into the femur 22 far enough to allow the bottom surface 26 of the collar 16 to contact the calcar area 20, as shown in FIG. 4D. However, in some cases, the tightness of the original press fit can decrease post-operatively, allowing the femoral hip implant 10 to subside further into the femur 22 and causing collar 16 to make contact with the calcar area 20 of the femur 22, as shown in FIG. 4E. This action arrests further subsidence of the femoral hip implant 10 into the femur 22 and aligns the porous surfaces of the second end and the collar with bone to facilitate bone ingrowth.

In some embodiments, the collar 16 can be fully porous, with the entire surface area of the collar 16 exhibiting porosity as shown in FIGS. 1-2. Porous surfaces exhibiting proper geometry can promote bone ingrowth, creating mechanical interlocking between the bone and the femoral hip implant 10. Such bone ingrowth improves the long term stability of the implant by reducing stress concentrations and bone resorption, as well as improving the torsional strength of the implant and reducing the likelihood of the need for revision surgery.

Figure 12:
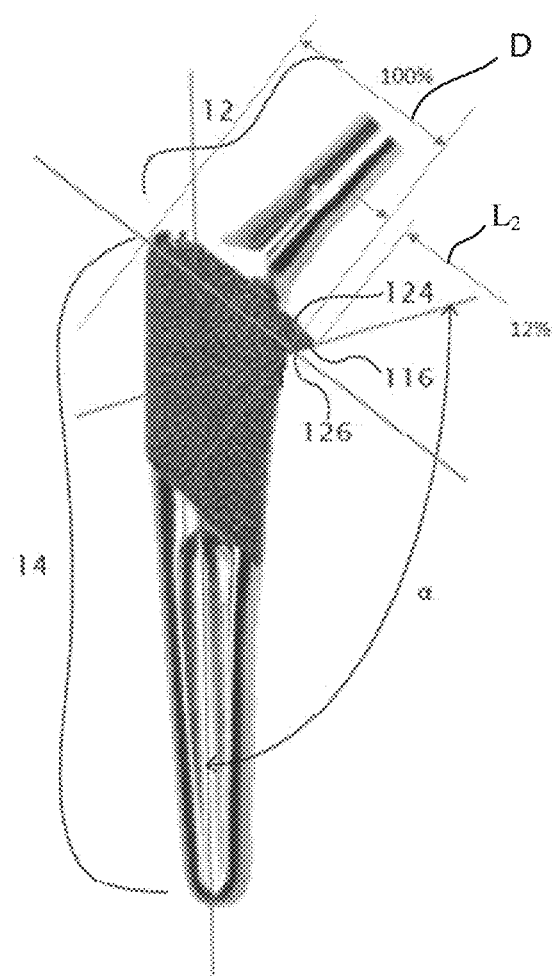
FIG. 12 is a side elevation view of the femoral hip implant of FIG. 10 illustrating a length of the collar.
Figure 13:
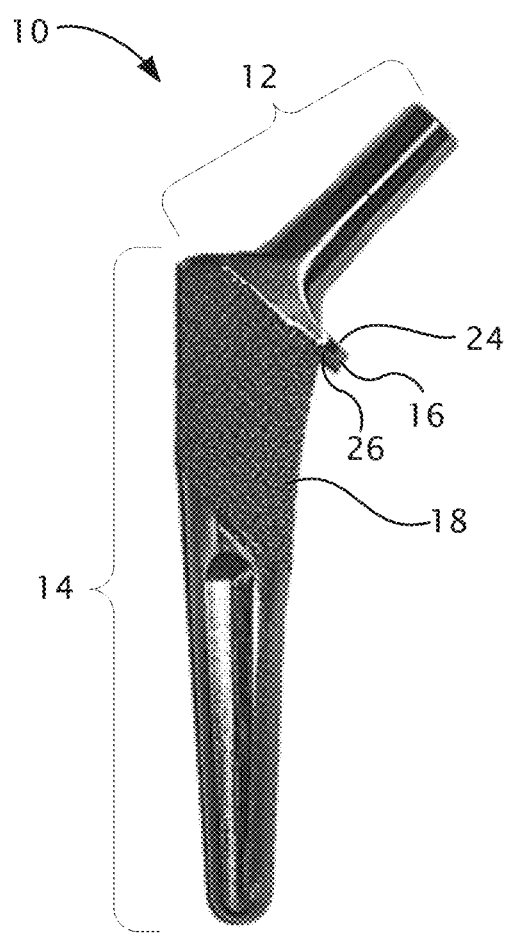
FIG. 13 is a side elevation view of another embodiment of a femoral hip implant.
Figure 14:
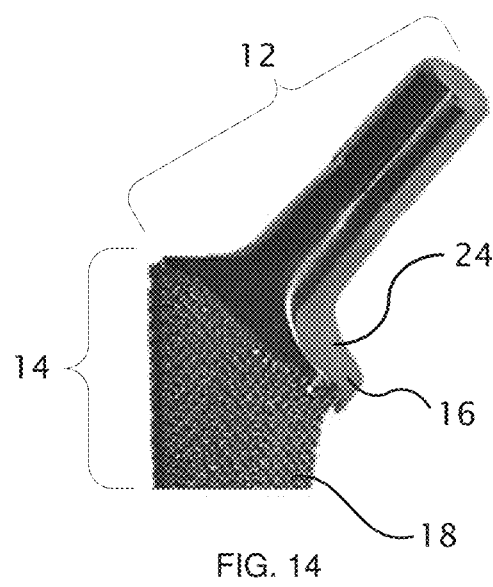
FIG. 14 is an enlarged isometric view of a portion of the femoral hip implant of FIG. 13.

In some embodiments, the top surface 24 of the collar 16 can comprise a solid (i.e., non-porous) metal surface or skin. The solid metal surface can be from about 0.005 inches to about 0.025 inches thick, and can further strengthen the collar 16. In other embodiments, the thickness of the metal at top surface 24 (the surface facing away from the femur 22) can vary between between 0.005 inches to 0.08 inches thick, or more preferably between 0.01 to 0.06 inches thick. An embodiment with the top surface 24 being formed with a metal surface (e.g., a thin metal "skin") is shown in FIGS. 12 and 13. All of the side of the collar 16 can be formed with a porous surface as shown in FIG. 1; alternatively, all or some of the side of the collar 16 can be formed with a non-porous metal surface as shown in FIG. 14. In either embodiment (FIG. 1; FIG. 12), the lower surface (i.e., the bone-contacting surface as shown in FIG. 3) of collar 16 is preferably formed with a porous surface that can promote bone ingrowth as discussed above.

Figure 11:
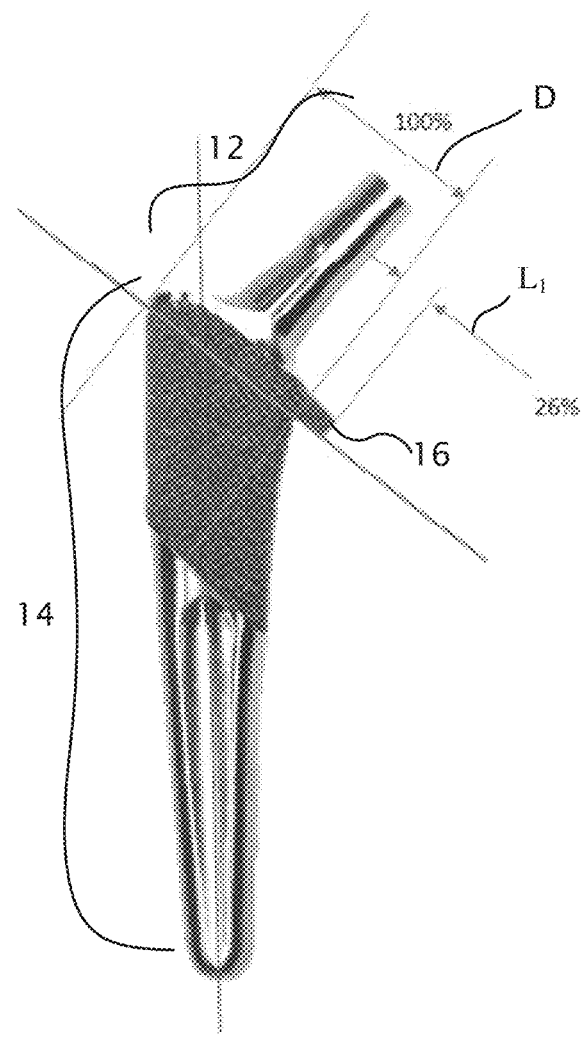
FIG. 11 is a side elevation view of the femoral hip implant of FIG. 1 illustrating a length of the collar.

In some embodiments, the length $L_1$ of the collar 16 can be related to a cross-sectional dimension D of the second end 14, as shown in FIG. 11. The length $L_1$ of the collar 16 can be from about 12% to about 26% of the cross-sectional dimension D of the second end 14. In some embodiments, the length $L_1$ of the collar 16 can be about 26% of the dimension D of the second end.

The femoral hip implant 10 described herein can be formed of various biocompatible materials. In some embodiments, the femoral hip implant 10 can be formed of titanium alloys, such as ASTM F-136 (Ti6Al4V ELI Titanium Alloy). In other embodiments, the implants can be formed using other biocompatible materials, such as cobalt chromium, stainless steel, and various composite materials or plastics.

Existing art implants require that the implant comprise multiple parts joined together to achieve a porous surface on both the collar and tapered body of the implant. However, using additive machining techniques such as electron beam melting (EBM) or laser sintering, the femoral hip implant 10 can be made from a single piece of material. In the case of the EBM technique, the implant can be produced by building the implant layer-by-layer from metal powder (e.g., a titanium alloy powder) using a powerful electron beam. In the case of the laser sintering technique, a high-powered laser is used to fuse beads of material to form the desired three-dimensional structure. These techniques can be used to produce an implant with the desired porous surfaces, allowing the porous surface of the femoral hip implant 10 to extend from the porous region 18 of the second end 14 to cover the entire surface area of the collar 16, as shown in FIGS. 1-2.

Figure 5:
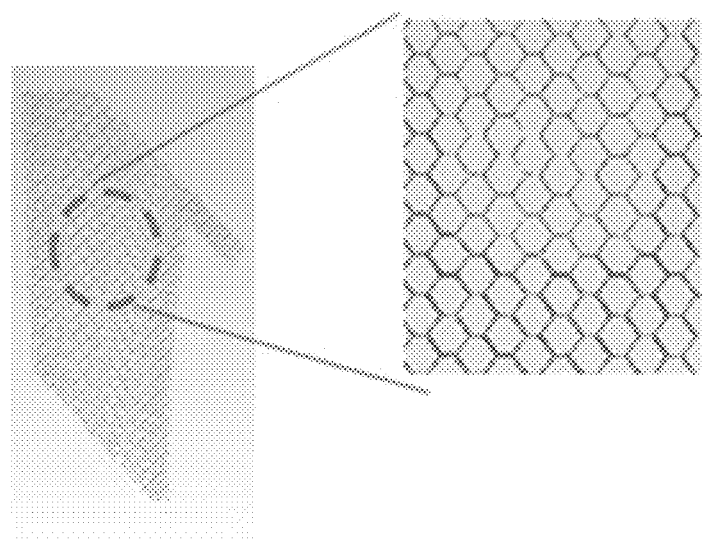
FIG. 5 is a representation of the geometric pattern of a porous surface.
Figure 6:
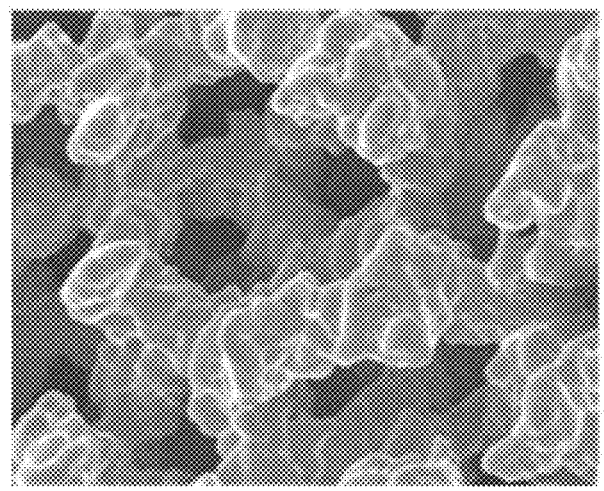
FIG. 6 is a micrograph of the geometric pattern of a porous surface.
Figure 7:
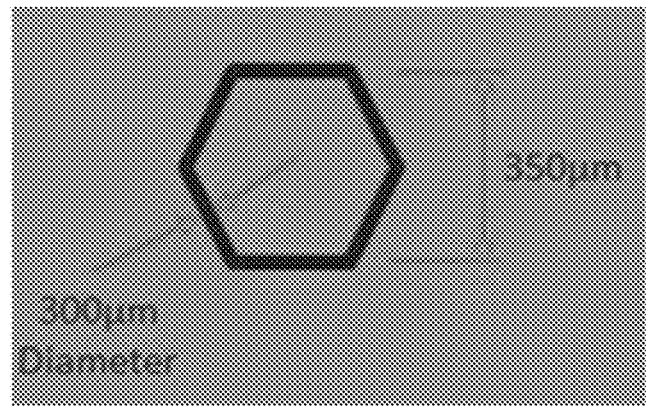
FIG. 7 is a front view of a diamond cubic unit cell geometry of a porous surface of a femoral hip implant.

The porosity of the femoral hip implant 10 is generally of a diamond cubic unit cell geometry, as shown in FIGS. 5-6, although any geometry creating a three-dimensional structure of sufficient porosity to allow bone ingrowth may be used. In some embodiments, the diamond cubic unit cell geometry comprises a 7-14 diamond cubic unit cell structure with approximately sixty-five percent of the interior volume comprising space and thirty-five percent comprising solid material. Although any ratio of space to solid material may be used, in some embodiments this ratio can comprise a majority of space as compared to solid material. In some embodiments, the diameter of the diamond unit cell structure is approximately 300 µm and the height is approximately 350 µm, with a pore size ranging from approximately 350-700 µm, as shown in FIG. 7. In some embodiments, the thickness is approximately 1000 µm, although any effective thickness may be used. Porosity of this size promotes bone ingrowth with sufficient vascularity to the underlying bone without compromising the structural integrity of the collar 16 under load.

Figure 8:
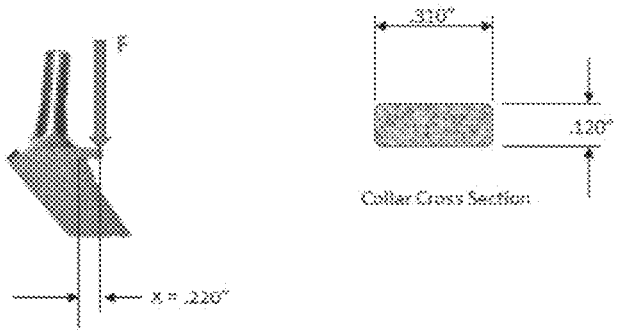
FIG. 8 is a diagram showing cross-section of a collar and application of a force to the collar.
Figure 9:
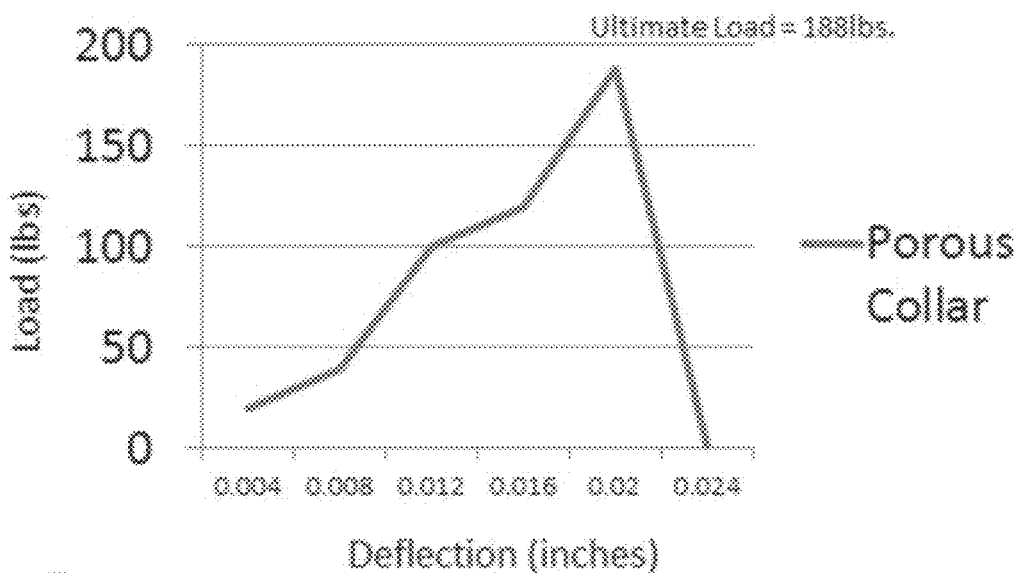
FIG. 9 is a diagram showing the deflection of a collar under load.

An additional feature of the collar 16 is its greater ability to elastically deflect under load compared to existing art solid collars with porous or textured surface treatments. The porosity of the collar 16 increases the elastic deflection of the collar 16 when subjected to loading by reducing the ultimate strength of the collar 16. Existing art collars fabricated from ASTM F-136 (Ti6Al4V ELI Titanium Alloy) with cross-sections of 0.310 inches by 0.120 inches exhibit an ultimate material stress of approximately 138,000 pounds per square inch with a fracture force of approximately 466 pounds. Such existing art solid collars generally are too stiff to deflect under normal loading conditions induced in femoral implants, leading to stress disuse bone resorption in the calcar area and destabilization of the implant. However, in some embodiments of the femoral hip implant 10, the collar 16 exhibits an ultimate material stress of approximately 48,000 pounds per square inch and a fracture load of approximately 163 pounds with a cross-section of 0.310 inches by 0.120 inches, as shown in FIG. 8. This reduction in the ultimate material stress and fracture force caused by the porosity of collar 16 in turn causes increased elastic deflection of collar 16 under load. As can be seen in FIG. 9, elastic deflection of collar 16 ranges from less than 0.004 inches to nearly 0.020 inches as a load ranging from 0 pounds to 188 pounds is applied. This elastic deflection of collar 16 can stimulate bone regeneration around collar 16, promoting bone ingrowth and long-term stabilization of the femoral hip implant 10.

Figure 10:
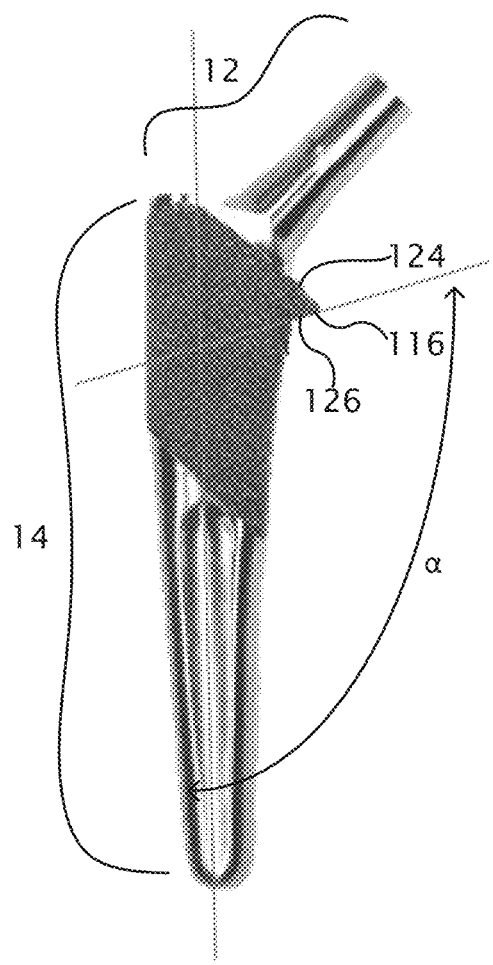
FIG. 10 is a side elevation view of a femoral hip implant having an alternative embodiment of a collar.

Referring now to FIG. 10, there is shown an alternative embodiment of a collar 116. The collar 116 can have a top surface 124 and a bottom surface 126, and can be positioned between the first and second ends 12, 14 of the implant 10, similar to the collar 16 of FIG. 1. The collar 116 can also have an entirely porous surface to promote bone ingrowth. As shown in FIG. 10, the bottom surface 126 of the collar 116 can form an angle α with a longitudinal axis of the implant. In some embodiments, the angle α can be from about 45 degrees to about 130 degrees. In some embodiments, the angle α can be about 110 degrees, and the collar 116 can have a generally tapered shape corresponding to the angle α. In this manner, the bending stress experienced by the collar 116 in use can be further reduced.

In some embodiments, the top surface 124 of the collar 116 in FIG. 10 can comprise a solid (i.e., non-porous) metal surface similar to the alternative embodiment of FIG. 1 discussed above. In some embodiments, the length L2 of the collar 116 can be related to the cross-sectional dimension D of the second end 14, as shown in FIG. 12. The length L2 of the collar 116 can be from about 12% to about 26% of the cross-sectional dimension D of the second end 14, similar to the collar of FIG. 1. In some embodiments, the length L2 of the collar 16 can be about 12% of the dimension D of the second end, as shown in FIG. 12. In this manner, the bending stress experienced by the collar 116 in use can be further reduced.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. I therefore claim as my invention all that comes within the scope and spirit of these claims.

I claim:

1. A bone implant apparatus comprising:
   a first end having a smooth surface configured to inhibit bone ingrowth;
   a second end extending from the first end in a non-coaxial fashion, the second end having an exterior surface, the exterior surface comprising at least a porous portion to allow bone ingrowth; and
   a collar located between the first end and the second end, the collar comprising a semicircular projection projecting from a front side of the second end in a direction substantially normal to the second end such that the collar does not project radially outward around the entire circumference of the apparatus;
   wherein the collar comprises a top surface and a bottom surface, the top surface comprising a flat top portion perpendicular to the first end, the bottom surface comprising a flat bottom portion that forms an angle with a longitudinal axis of the second end,
   wherein both the flat top portion and the flat bottom portion are porous to allow bone ingrowth, and wherein the porous portion of the second end, the flat bottom portion and the flat top portion form a continuous porous surface,
   wherein the second end comprises a rear side that is generally straight and an edge of the porous portion extends downward at an angle from the rear side to the front side,
   wherein the flat bottom portion intersects the exterior surface of the second end at a boundary line, and
   wherein the collar defines a length from the boundary line to an outmost peripheral edge of the collar, and the second end defines a cross-sectional dimension from the boundary line to an opposing edge of the second end along a direction perpendicular to the first end, wherein the length of the collar ranges from 12% to 26% of the cross-sectional dimension of the second end, and
   wherein the opposing edge of the second end is at the rear side of the second end.

2. The bone implant apparatus of claim 1 is made from a single piece of material such that the first end, the collar and the second end form an integral piece without joints.

3. The bone implant apparatus of claim 1, wherein the second end defines a tapered segment extending away from the porous portion of the second end, wherein the first end defines a centerline that intersects with a point on the porous portion of the second end, and the porous portion of the second end extends beyond the point towards the tapered segment.

4. The bone implant apparatus of claim 1, wherein the collar further comprises one or more side surfaces joining the top surface and the bottom surface, wherein at least some of the side surfaces are porous to allow bone ingrowth.

5. The bone implant apparatus of claim 4, wherein all side surfaces are porous to allow bone ingrowth.

6. The bone implant apparatus of claim 1, wherein the flat top portion and the flat bottom portion are parallel to each other.

7. The bone implant apparatus of claim 1, wherein the angle ranges from 45 degrees to 130 degrees.

8. The bone implant apparatus of claim 1, wherein the angle is about 110 degrees.

9. The bone implant apparatus of claim 1, wherein the flat bottom portion and the exterior surface of the second end form an acute angle at the boundary line.

10. The bone implant apparatus of claim 1, wherein the flat bottom portion and the exterior surface of the second end form an obtuse angle at the boundary line.

11. The bone implant apparatus of claim 1, wherein the flat top portion and the flat bottom portion intersect at an edge spaced away from the boundary line such that the collar has a tapered shape with a thickness of the collar increasing linearly from the edge to the boundary line.

12. The bone implant apparatus of claim 1, wherein the continuous porous surface comprises a solid material configured in a diamond cubic unit cell geometry, wherein the diamond cubic unit cell geometry comprises between 7 and 14 diamond unit cell structures.

13. The bone implant apparatus of claim 12, wherein the diamond unit cell structure has a pore size ranging from 350 μm to 700 μm.

14. The bone implant apparatus of claim 1, wherein the collar elastically deflects under load to stimulate bone growth.

15. The bone implant apparatus of claim 14, wherein the elastic deflection of the collar is between 0.004 inches and 0.02 inches when subjected to a load of 188 pounds.

* * * * *